United States Patent [19]
Johnston

[11] 3,933,155
[45] Jan. 20, 1976

[54] PRESSURE INJECTOR APPARATUS HAVING IMPROVED TRIGGER MECHANISM

[75] Inventor: Charles Johnston, Roanoke, Va.

[73] Assignee: Mizzy Inc., Clifton Forge, Va.

[22] Filed: Jan. 23, 1975

[21] Appl. No.: 543,438

[52] U.S. Cl...... 128/173 H; 128/239 R; 425/145 R; 118/3 R; 239/63 R; 401/279
[51] Int. Cl.² .......................................... A61M 5/30
[58] Field of Search ........ 128/173 H, 173 R, 213 R, 128/215 R, 239; 425/DIG. 225, 145, 146; 118/3 R, 8 R; 239/63 R; 401/206, 264, 279

[56] References Cited
UNITED STATES PATENTS

| | | | |
|---|---|---|---|
| 3,189,029 | 6/1965 | Stephens | 128/173 H |
| 3,730,180 | 5/1973 | Davidson | 128/145.6 |
| 3,742,899 | 7/1973 | Alperin et al. | 118/8 |
| 3,874,380 | 4/1975 | Baum | 128/215 |

FOREIGN PATENTS OR APPLICATIONS 1,049,564    8/1953    France .......................... 128/173 H Primary Examiner—Robert W. Michell
Assistant Examiner—Henry J. Recla
Attorney, Agent, or Firm—Arthur B. Colvin

[57] ABSTRACT

The present invention relates to a pressure injection mechanism of the type which, when triggered, expresses predetermined dosages of liquid under high pressure from a dosage orifice at speeds enabling the same to penetrate an injection site which may be the skin of a human or an animal, the stalk or other surface of a plant and so forth. The apparatus is characterized by a novel triggering mechanism which assures that the apparatus may be triggered to effect a dosage administering cycle only when the dosage orifice is positioned against the injection site with a predetermined orientation. Furthermore, the triggering device, by preventing triggering unless proper orientation is achieved, enables the provision of a multiple dosage uniit wherein two or more dosages may be simultaneously administered into the same or different injection sites, administration of the dosages by triggering of the mechanism being possible only if both of the injection sites are in proper dosage receiving relationship to the apparatus.

7 Claims, 7 Drawing Figures

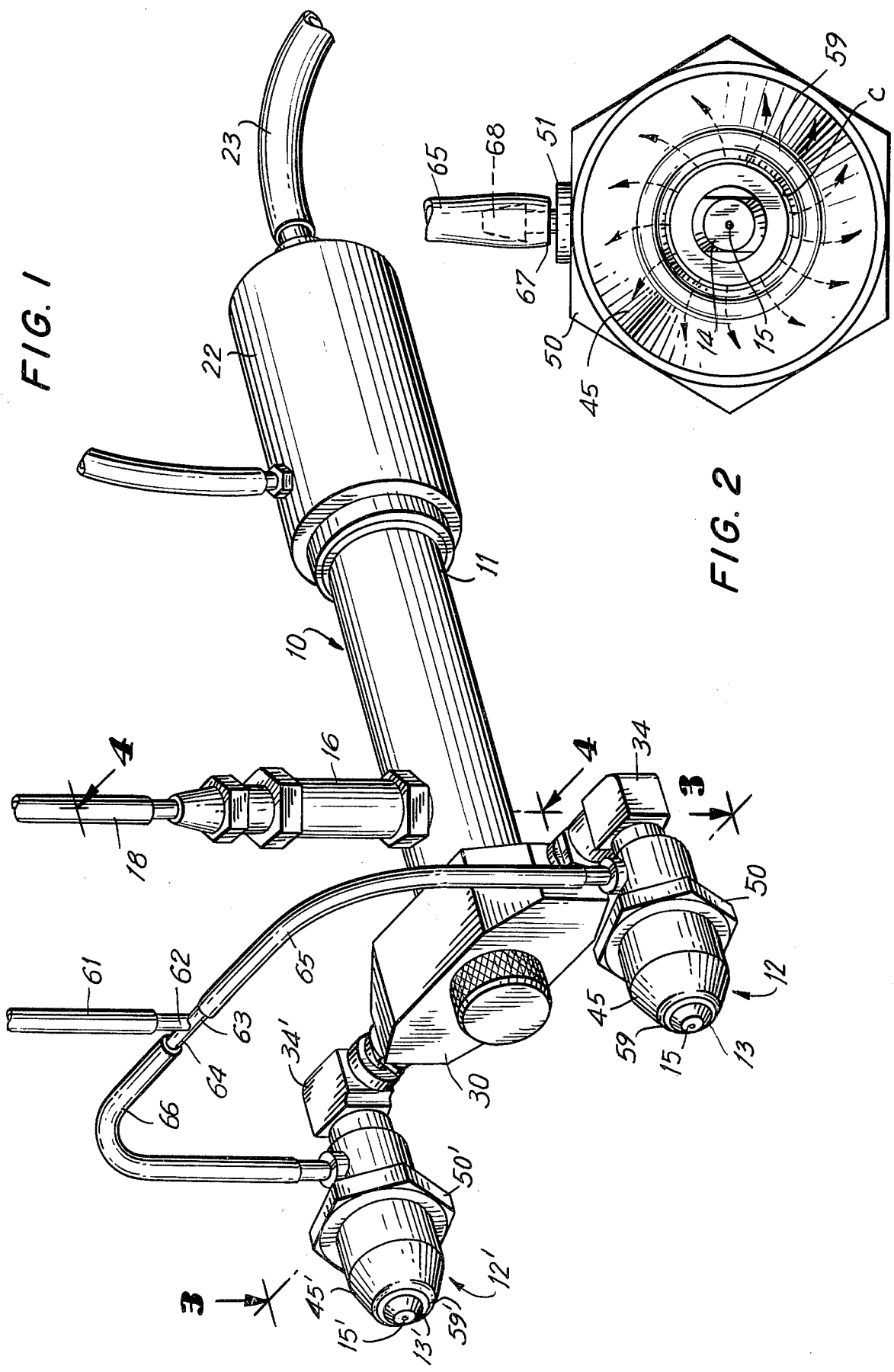

PRESSURE INJECTOR APPARATUS HAVING IMPROVED TRIGGER MECHANISM

BACKGROUND OF THE INVENTION

1. Field of the Invention

The present invention is in the field of pressure injectors, relating particularly to a mechanism for introducing effective dosages of liquid medicament into the skin of a human or an animal or the stalk or other surface of a plant and so forth without the use of hypodermic needles.

2. The Prior Art

It is known, in lieu of hypodermic needles, to administer dosages by directing a stream of medicament, for example, under high pressure against the skin of the subject.

As pointed out in co-pending application Ser. No. 380,357, now U.S. Pat. No. 3,859,996, the total amount of fluid expelled from the dosage orifice may not be effectively introduced into the body of the subject. Additionally, the depth of penetration and the direction of penetration of a dosage into a subject varies the physiological effect of the medication on the subject. As further noted in the above mentioned application, the effective dose administered may depend on the angle of the orifice with respect to the subject at the instant of transfer, as well as the pressure with which the orifice contacts the subject.

In the aforementioned application there is disclosed a novel triggering mechanism for a pressure inoculator which prevents discharge of the apparatus unless portions of the apparatus are positioned against the skin surface of the subject. The device, to a degree, tends to aid in the orientation of the orifice relative to the surface of the subject.

SUMMARY

The present invention is directed to an improved injector of the pressure jet type, characterized by a novel triggering mechanism which permits discharge of the apparatus only when the apparatus is held against the subject with a predetermined orientation and more particularly is substantially perpendicular to the skin surface of the subject. As a result of the improved triggering apparatus, it is possible simultaneously to dose two or more uncooperative subjects, triggering being automatically effected responsisve to the proper positioning of the subjects relative to the nozzle assembly.

The nozzle assembly and the triggering components thereof are so connected and arranged that the injecting cycle cannot be initiated unless all recipients are properly positioned.

The invention further relates to an improved triggering nozzle assembly for a device of the type described which may be manually adjusted to vary the pressure with which the apparatus must be forced against the subject before a discharge cycle is initiated.

In accordance with the invention, the dosage nozzle or orifice projects forwardly through the open mouth portion of an otherwise sealed chamber, there being defined between the orifice and the mouth portion an annular or parti-annular space.

A source of trigger air under predetermined pressure is introduced into the chamber, from which it leaks or escapes to the atmosphere through the space in the mouth surrounding the discharge orifice.

When the nozzle assembly is positioned against the skin of the subject, the discharge orifice first engages the subject since it is the forwardmost portion of the nozzle. As the nozzle is pressed against the subject with progressively increasing force, which may be extremely slight, the skin of the subject is deformed and flows or molds around the nozzle so as to seal or partially seal the mouth portion of the chamber surrounding the nozzle.

Means are provided to sense pressure build-ups in the trigger air supply and to trigger the injector through an operative cycle only where pressure build-up of a predetermined magnitude is sensed. Such build-up is, in turn, possible only when the nozzle has been pressed against the skin to a sufficient depth to permit the surrounding skin surface to seal the chamber.

The apparatus is suitable for use in an injector for simultaneously dosing two or more subjects by providing multiple nozzles with a common trigger air supply so connected that leakage to the atmosphere may be effected between alternate paths defined between the subjects and the nozzle assemblies, whereby triggering will be possible only after all nozzle assemblies have been appropriately sealed.

By varying the amount by which the orifice extends forwardly of the mouth portion, there is automatically varied the pressure necessary to seal the mouth portion surrounding the orifice.

By providing a continuous trigger air bleed area or areas surrounding the nozzle, or by providing leakage paths ringing the nozzle each of which must be sealed to achieve the requisite pressure increase, there is assured a precise perpendicularity between the orifice and the subject, it being appreciated that any tilting will permit a leakage between the noted parts.

Accordingly, it is an object of the invention to provide a pressure injector mechanism having an improved triggering device.

It is a further object of the invention to provide an improved triggering device for a pressure injector mechanism wherein administration of a dose can be effected only after the apparatus is positioned against the recipient so that there exists a substantial perpendicularity between the recipient's skin portion and the injector.

Still a further object of the invention is the provision of an injector of the type described having multiple nozzles fed with dosages from a common dosage supply chamber, the nozzles each including mutually interconnected triggering circuits whereby a dosage can be administered only when each of the nozzles is properly positioned against a subject.

To attain these objects and such further objects as may appear herein or be hereinafter pointed out, reference is made to the accompanying drawings in which:

FIG. 1 is a perspective view of an injection apparatus in accordance with the invention;

FIG. 2 is a magnified front elevational view of an injector nozzle assembly;

Figure 4:
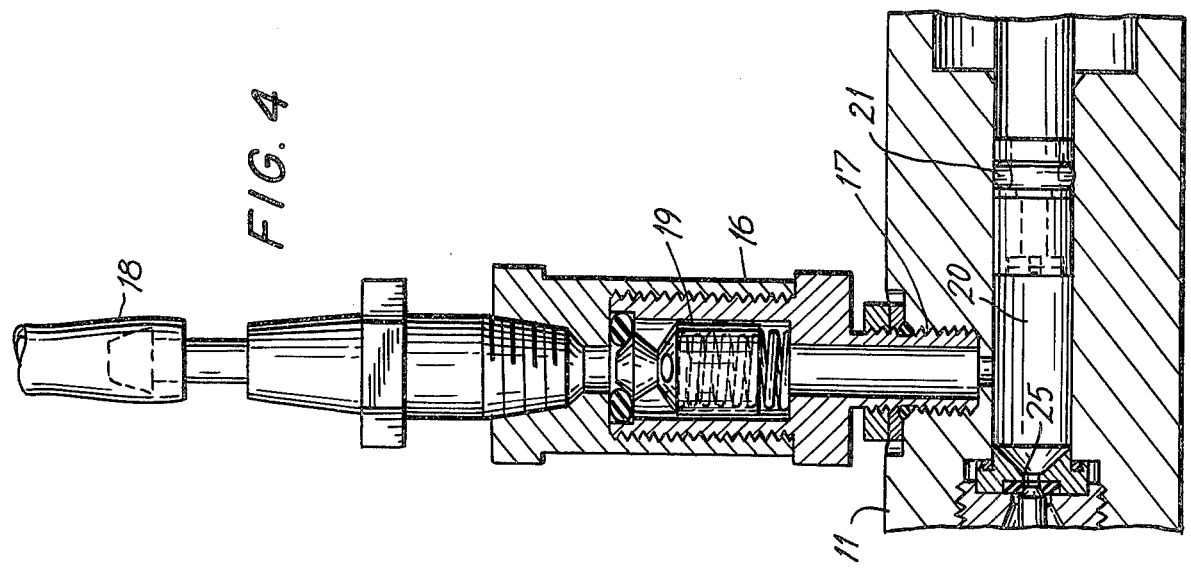
FIG. 4 is a vertical section taken on the line 4—4 of FIG. 1.

Referring now to the drawings, there is shown in FIG. 1 an injector mehcanism 10 comprising generally a body portion 11 having a pair of injector nozzle assemblies 12, 12' at one end thereof. While the illustrated embodiment discloses a dual system wherein there are provided separator injector nozzel assemblies 12, 12' for the simultaneous inoculation of two subjects, such as fowl, livestock, etc., it will be readily recognized that certain of the benefits of the instant invention will be realized in connection with a single nozzle device.

The high pressure injector of the instant invention, as is the case with the aforementioned copending application, includes a discharge nozzle 13 having an external face 14. A discharge orifice 15 is through the nozzle 13, said orifice opening at the face 14. Responsive to operation of the device, a plunger mechanism hereinafter generally described drives a predetermined quantity of medicament outwardly through the discharge orifice 15. Since the nozzle assemblies 12 and 12' are identical, a description of one will suffice.

As the means for supplying medicament doses under high pressure to the nozzles 12, 12' is fully and completely disclosed in the aforementioned application, now U.S. Pat. No 3,859,996, dated Jan. 14, 1975, detailed discussion thereof will not be here repeated. It is considered sufficient of note that a nipple assembly 16 is threaded into an inlet supply port 17 formed in the body 11 of the injector mechanism. The inlet nipple is connected through a conduit 18 to a source of medicament, a one way valve 19 being interposed between the conduit 18 and port 17.

20 is a chamber formed in the body portion 11, which chamber is filled with a measured dose of medicament responsive to retraction of the expulsion piston 21. A piston drive mechanism is located in the drive chamber 22, the drive mechanism being powered by compressed air or a like power source admitted to the chamber 22 through the conduit 23. A control or triggering assembly 24 initiates an operative cycle, as more fully explained hereinafter.

In the loading portion of the cycle, piston 21 is shifted to the right to the position shown in FIG. 4, which movement is accompanied by the introduction of medicament fluid through conduit 18 past one way check valve 19 and into the reservoir or chamber 20. Upon triggering of an administering cycle, piston 21 is driven from right to left, displacing under high pressure medicament contained in the chamber 20. As more fully set forth in the copending application aforementioned, the dosage administered is a function of the amount of retractile (rightward) movement of the piston 21, and means are provided to control the stroke length and hence the dosage.

Fluids emerging from the chamber 20 pass through conduit 25, unseating high pressure check valve 26, whereupon they are admitted to discharge conduit 27. In the illustrated embodiment, the conduit 27 leads to a T connection 28, the branches of the T leading respectively to discharge conduit branches 29 and 29' which are operatively connected to discharge orifices 15, 15', respectively.

The branches 29, 29' are formed in a yoke 30 threadedly connected at 31 to a complemental fitting 32 formed on the body portion 11. The yoke includes sidewisely open discharge ports 33, 33', within which ports are mounted the L shaped nozzle receiver conduits 34, 34'.

The nozzle receiver conduits include internal bores 35, 35', respectively, extending from the branches 29, 29' operatively connected to receive the ejected medicament, to a threaded nozzle assembly receiver fitting 36, 36'.

The nozzle assembly 12 includes a plug member 37 having an extending threaded tailpiece 38 received on the complementally threaded fitting 36. An O ring 39 or like gasket is tightly sandwiched between the rearwardly facing annular shoulder 40 of the plug 37 and the forwardly facing shoulder 41 of the conduits 34. The plug 37 includes an axially extending discharge conduit 42 which, in the connected position, forms a continuation of the conduit 35. The plug 37, adjacent its outer end, includes an internally threaded bore 43, within which bore is threadedly connected the discharge nozzle 13, suitable packing or gasketing 44 being compressed between the discharge nozzle and the plug 37.

From the arrangement as thus far described, it will be understood that when medicament is expelled from the chamber or reservoir 20 under the influence of the drive piston in the course of an operative stroke, the same unseats the high pressure check valve 26 passing to conduit 27, branches 29, 29' and then to the discharge nozzles 15, 15' through the medium of connecting passages 30, 35, 42.

The present invention is directed principally to the improved means for triggering an operative or administering cycle.

Figure 3:
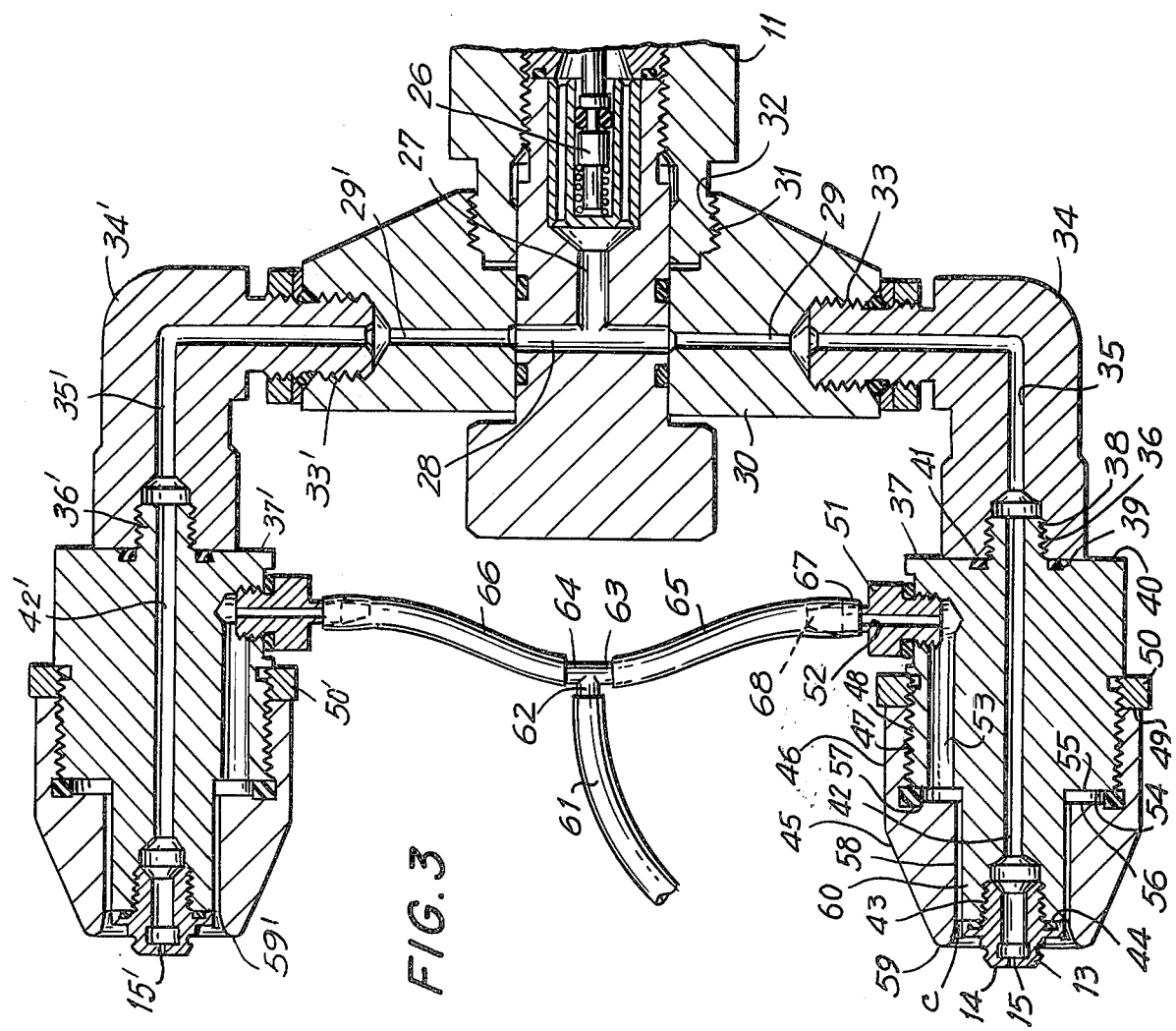
FIG. 3 is a section taken on the line 3—3 of FIG. 1.

Referring particularly to FIG. 3, the triggering means includes an annular collar member 45 having its inner end 46 internally threaded as at 47, the threaded portion 47 being engaged with a complemental external thread 48 formed on the plug 37. It will be appreciated that by rotation of the collar 45, the same may be shifted axially forwardly and rearwardly relative to the plug 37.

The collar 45 preferably carries at its trailing end 49 a resilient, deformable gasket 50 which is threaded or deformed by the threads 58. The gasket 50 functions both as a pressure seal and as a means for frictionally resisting rotation of the collar relative to the plug 37.

As more fully set forth hereinafter, forward and rearward movement of the collar 45 relative to the plug 37 functions to control the pressure with which the outer face 14 of the discharge nozzle must be pressed against the subject in order to trigger an operative cycle.

Plug 37 includes a nipple 51 having an internal air conduit 52 leading to an exially extending air bleed bore 53. The bleed bore 53 opens to an annular space 54 defined between annular shoulder 55 of the plug 37 and rearwardly facing shoulder 56 formed on the collar 45. A sealing 0 ring or gasket 57 is preferably disposed between the collar and the plug.

The collar 45 includes an axially extending bore 58, terminating in a rim or mouth portion 59. The plug 37 includes a cylindrical extension 60 lying within the bore 58, the extension 60 and bore 58 being so dimensioned as to provide an annular space or chamber C between the plug and the collar. It will be appreciated that the chamber C opens outwardly at the mouth 59.

A source of trigger air is connected to the nozzle assemblies 12, 12' through the trigger air conduit 61. The conduit 61 includes a T fitting 62, the branches 63, 64 of which are connected to nozzles 12, 12' by trigger air branch conduits 65, 66, respectively. The end 67 of conduit 65 remote from fitting 62 is sleeved over an enlarged head portion 68 in the nipple 51.

Operation of the device will be apparent from the preceding description.

Trigger air conduit 61 is connected to the control assembly 24 which provides a source of trigger air under low pressure. The control assembly includes a pressure sensing mechanism operatively connected with the line 61, which mechanism is known per se, and which is connected to trigger the apparatus through an operative cycle responsive to a sensed pressure build-up of a predetermined magnitude in the line 61.

As may be perceived from an inspection of FIG. 3, air admitted through conduit 61, passing through branches 65, 66, is permitted to flow through the bore 53 and annular chamber defined between the collar 45 and plug 37, out of the mouth 59 into the atmosphere. So long as the trigger air is permitted to bleed continuously to the atmosphere no pressure build-up is possible within the conduit 61. It is only when the mouth portion 59 of the nozzle assembly 12 and 59' of the nozzle assembly 12' are sealed or substantially sealed that such pressure build-up can take place. From an inspection of the illustrated embodiment, it will be appreciated that unless both of the mouth portions 59 and 59' are sealed, pressure build-up will not be permitted since the two mouth portions provide alternate access to the atmosphere.

Figure 7:
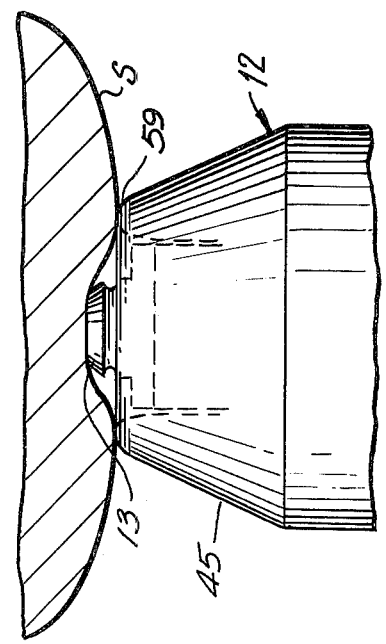
FIGS. 6 and 7 are enlarged diagrammatic views of the positions of the nozzle relative to the epidermis of the subject respectively in the space and contacting or operative positions of the injector mechanism.
Figure 5:
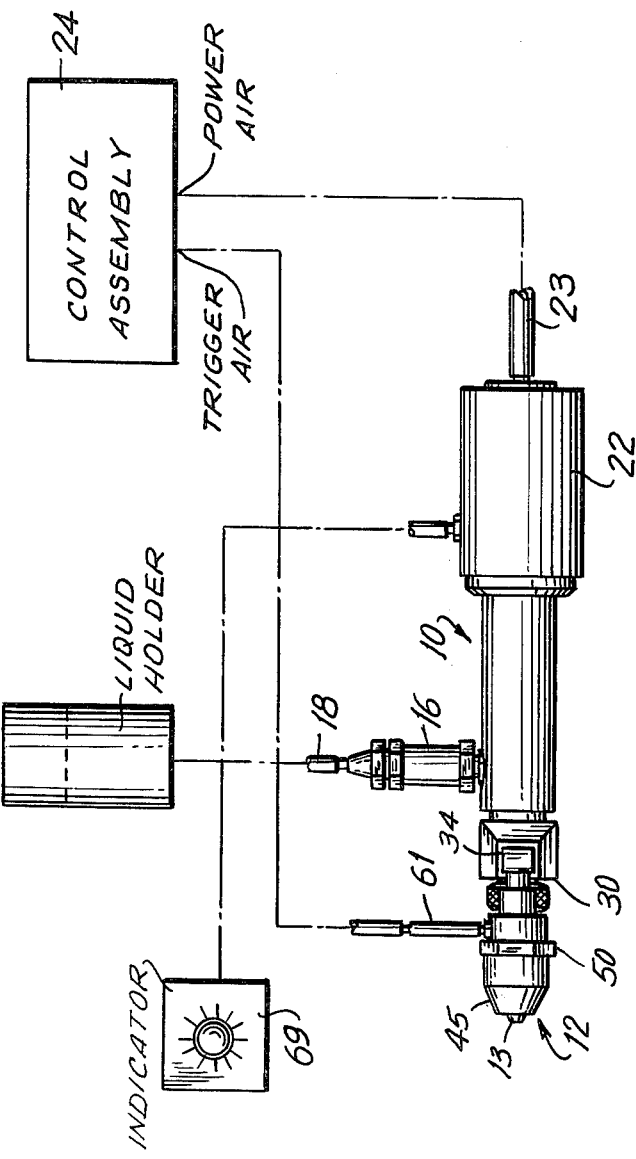
FIG. 5 is a schematic view of the injector mechanism and its connections with the various supply and control mechanisms.
Figure 6:
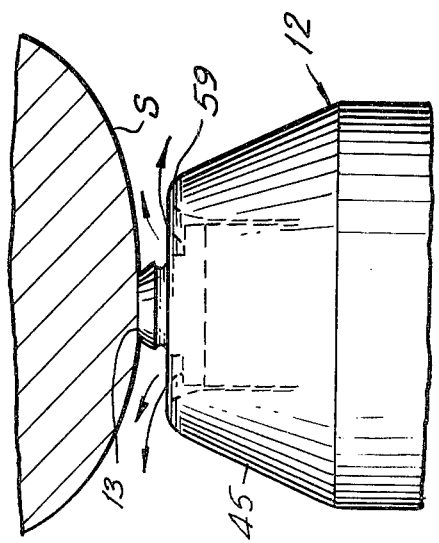

Referring now to FIGS. 6 and 7, wherein the legend S denotes a subject to be dosed, it will be seen that when the nozzle 13 is touched against the subject, bleed air is still permitted to flow outwardly in the area between the mouth 59 and the subject. It is only when the nozzle assembly 12 has been pressed sufficiently against the subject (see FIG. 7) that the skin of the subject is sufficiently indented by nozzle 13 that the skin rolls or folds into contact with the mouth 59 surrounding the nozzle 13 that a seal of the mouth may be effected.

As previously noted, in a multiple dosing apparatus both the mouth 59 and the mouth 59' must be sealed before pressure build-up sufficient to trigger an operative cycle is developed in the conduit 61.

Several important advantages derive from the use of the assembly described.

Since the trigger air is free to bleed to the atmosphere, if any portion of the mouth 59' is unsealed, the described assembly precludes the possibility of triggering when the nozzle is tilted relative to the subject. In the event of any such tilt, a seal might be formed to one side of the mouth of a nozzle assembly but other portions of the nozzle would be spaced from the subject, thereby providing passage for air escape.

The pressure which is required to be exerted before sealing of the mouth portions 59, 59' is varied by threading the collar 45 forwardly and rearwardly with respect to the plug 37. If, by way of example, the collar is threaded forwardly so that the face 14 of the discharge nozzle is flush with the plane of the mouth 19', the skin of the subject will seal the mouth with only a relatively minor pressure, since little or no skin indentation is required to effect such seal. If, on the other hand, the collar is threaded rearwardly to increase the projection of the discharge nozzle forwardly of the mouth 59, it will be apparent that the force necessary to embed the discharge nozzle deeply enough into the subject to permit the surrounding skin to form a seal will be substantially greater.

In the double headed device illustrated, inoculation of two fowl, for instance, may be readily accomplished by fixing the position of the injector apparatus and manually moving the fowl against the nozzle assemblies 12, 12'. Since the apparatus may not be triggered until both mouths 59, 59' are sealed, the task of the operator is greatly simplified as he need not carefully position the fowl relative to the nozzles but is assured by the triggering of an operative cycle that proper positioning was effected.

Optionally, the device incorporates an indicator 69, such as a light, which flashes or otherwise signals the operator that a dose administering cycle has been completed.

While the device has been illustrated in connection with a two headed apparatus, it will be readily apparent that the utility thereof is not so limited. It is feasible to employ a single headed unit, for example, and derive therefrom many of the benefits hereinabove discussed in detail.

Likewise, while the illustrated embodiment incorporates a continuous annular space for the escape of bleed air, whereby tilting of the device relative to the subject prevents actuation of the device, it will be understood that a configuration of escape passage which provides air exits at spaced points surrounding the discharge nozzle will function in the desired manner, whether or not the bleed passage is continuous.

From the foregoing it will be understood that there is provided automatic triggering mechanism for a pressure injector apparatus which assures that the apparatus cannot be discharged unless positioned against the subject, with a predetermined orientation. Furthermore, as the nozzle must be positioned against the subject for the dose to be injected, there is a reduced possibility of relative movement between the subject and the pressure device in the course of administration of the dose. This is an important factor since the jet emerging from the discharge orifice acts as a knife and relative movement in the course of its administration may result in substantial trauma to the subject.

Having thus described the invention and illustrated its use, what is claimed as new and is desired to be secured by Letters Patent is:

1. In a transdermal pressure injection mechanism including a body portion having a liquid reservoir, and discharge means for expelling predetermined dosages of liquid under high pressure from said reservoir to a discharge conduit, a self-triggering nozzle assembly fixed to an end of said body portion, said assembly comprising a collar member having an internal bore terminating in an outwardly facing mouth portion, a discharge nozzle mounted in said bore in spaced relation to said collar and extending substantially parallel thereto, said nozzle including a face portion projecting through said mouth portion, said nozzle including an orifice extending through said face portion and connected to said discharge conduit, said nozzle and collar defining therebetween a chamber opening outwardly through said mouth, trigger conduit means for introducing air under pressure into said chamber, and sensor means operatively connected to said trigger conduit means for energizing said discharge means to expel a dosage of liquid through said orifice responsive to a pressure variation of a predetermined magnitude sensed in said conduit means as a result of substantially sealing said mouth portion of said chamber by positioning of said mouth against an injection site.

2. Article in accordance with claim 1 wherein said nozzle and the mouth portion of said collar define therebetween a continuous circumferential space surrounding said nozzle whereby said chamber may be substantially sealed only when all portions of said space are pressed against the injection site.

3. Apparatus in accordance with claim 2 wherein said collar is circular in transverse section, said discharge nozzle is coaxially aligned with said collar, said nozzle and collar defining therebetween an annular space, the axis of said orifice coinciding with the axis of said collar.

4. Apparatus in accordance with claim 3 wherein said mouth portion is planar in transverse section.

5. Apparatus in accordance with claim 4 and including adjustment means interposed between said collar and discharge nozzle whereby the distance which said discharge nozzle projects beyond said mouth portion may be varied.

6. Article in accordance with claim 1 including adjustment means interposed between said collar and nozzle for varying the distance beyond said mouth portion which said nozzle projects and, hence, the pressure necessary substantially to seal said mouth portion.

7. Apparatus in accordance with claim 1 wherein said mechanism includes a plurality of said self-triggering nozzle assemblies in parallel spaced relation, and said trigger conduit means is operatively connected to the chambers of each of said conduit means, whereby the chambers of each of said nozzle assemblies must be substantially sealed in order to develop a pressure variation in said conduit means of the magnitude required to energize said sensor means.

* * * * *